(12) United States Patent
Hollinger et al.

(10) Patent No.: US 9,675,381 B2
(45) Date of Patent: *Jun. 13, 2017

(54) DUAL HEAD PEDI APPARATUS

(71) Applicant: E. MISHAN & SONS, INC., New York, NY (US)

(72) Inventors: Fred Hollinger, Monroe Township, NJ (US); Edward I. Mishan, New York, NY (US)

(73) Assignee: E. Mishan & Sons, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/152,382

(22) Filed: May 11, 2016

(65) Prior Publication Data

US 2017/0049476 A1    Feb. 23, 2017

Related U.S. Application Data (63) Continuation-in-part of application No. 14/828,900, filed on Aug. 18, 2015.

(51) Int. Cl.
| | | |
|---|---|---|
| *A61B 17/54* | (2006.01) | |
| *A61H 15/00* | (2006.01) | |
| *A61B 17/00* | (2006.01) | |
| *A61B 17/32* | (2006.01) | |

(52) U.S. Cl.
CPC ......... *A61B 17/54* (2013.01); *A61H 15/0085* (2013.01); *A61B 2017/00761* (2013.01); *A61B 2017/320008* (2013.01)

(58) Field of Classification Search
CPC ............... A61H 15/00; A61H 15/0078; A61H 15/0085; A61H 15/0092; A61H 15/02; A61H 2015/0007; A61H 2015/0014; A61H 2015/0021; A61H 2015/0028; A61H 2015/0035; A61H 2015/0042; A61H 2015/005; A61H 2015/0057; A61H 2015/0064; A61H 2015/0074; A61H 2201/1215; A61H 2201/14; A61H 2201/1645; A61H 2201/1647; A61H 2201/1692; A61B 17/54
See application file for complete search history.

(56) References Cited

U.S. PATENT DOCUMENTS

| | | | | |
|---|---|---|---|---|
| 2,275,498 A | * | 3/1942 | Berndt | ................. G03B 17/265 |
| | | | | 242/356.5 |
| 2,395,296 A | | 1/1945 | Schwab | |
| 2,867,214 A | | 1/1959 | Wilson | |

(Continued)

FOREIGN PATENT DOCUMENTS

| | | |
|---|---|---|
| DE | 29710333 U1 | 9/1997 |
| DE | 20104304 U1 | 5/2001 |

(Continued)

*Primary Examiner* — LaToya M Louis
(74) *Attorney, Agent, or Firm* — Notaro, Michalos & Zaccaria P.C.

(57) ABSTRACT

A handheld skin exfoliating apparatus has handle and head portions with two drums having different abrasiveness mounted on opposite sides of the head portion. A drive motor and gears are mounted to the handle and/or head portions and operatives to rotate the drums for exfoliate skin when a respective outer surface of one drum contacts the skin.

4 Claims, 7 Drawing Sheets

(56) References Cited

U.S. PATENT DOCUMENTS

| | | | | |
|---|---|---|---|---|
| 3,077,878 | A * | 2/1963 | Gerard | A61H 15/0085 601/113 |
| 5,311,860 | A * | 5/1994 | Doria | A61H 23/0254 601/103 |
| 6,471,712 | B2 | 10/2002 | Burres | |
| 8,508,815 | B2 * | 8/2013 | Kim | H04N 1/0402 318/685 |
| 8,551,117 | B2 | 10/2013 | Yiu | |
| 2004/0027009 | A1 * | 2/2004 | Ji | F04D 25/084 310/50 |
| 2004/0049136 | A1 * | 3/2004 | Lin | A61H 23/0254 601/86 |
| 2004/0167481 | A1 * | 8/2004 | Carlucci | A45D 26/0004 604/291 |
| 2004/0254587 | A1 | 12/2004 | Park | |
| 2007/0232966 | A1 * | 10/2007 | Applebaum | A61H 15/0085 601/17 |
| 2008/0167589 | A1 * | 7/2008 | Fung | A61H 23/0254 601/104 |
| 2010/0049106 | A1 * | 2/2010 | Gueret | A45D 34/041 601/112 |
| 2010/0179460 | A1 * | 7/2010 | Tsai | A61H 7/004 601/134 |
| 2011/0052261 | A1 * | 3/2011 | Fukushima | G03G 15/5008 399/167 |
| 2011/0087141 | A1 * | 4/2011 | Wagy | A61H 15/0085 601/137 |
| 2011/0230804 | A1 | 9/2011 | Serhan | |
| 2012/0226289 | A1 | 9/2012 | Yiu | |
| 2012/0323257 | A1 | 12/2012 | Sutton | |
| 2014/0288473 | A1 * | 9/2014 | Matsushita | A61H 15/00 601/137 |
| 2016/0151234 | A1 * | 6/2016 | Chen | A61H 15/0078 601/113 |

FOREIGN PATENT DOCUMENTS

| | | |
|---|---|---|
| EM | 1421689 | 9/2014 |
| WO | 2014118577 A1 | 8/2014 |

* cited by examiner

DUAL HEAD PEDI APPARATUS

CROSS REFERENCE TO RELATED APPLICATION

This is a continuation-in-part application of U.S. patent application Ser. No. 14/828,900 filed Aug. 18, 2015, and incorporated herein by reference.

FIELD AND BACKGROUND OF THE INVENTION

The present invention relates generally to the field of personal grooming, and in particular, to a new and useful dual head pedi apparatus to be used, for example, to exfoliate a user's feet.

U.S. Pat. No. 8,551,117 discloses a handheld exfoliating device for removing skin, e.g. from the bottom of the feet of a user, using a single drum having an abrasive outer surface to abrade the skin of the user during rotation of the drum.

Published international patent application WO 2014/118577 discloses a dermabrasion device for removing a hard, dry skin layer on a surface of the foot, that has a single concave or convex drum with an abrasive surface.

Since such devices are used most often by a user to exfoliate the feet, they are sometimes called a pedi. All such devices offer a user one drum at a time to exfoliate the skin, using one level of abrasion. A need remains for an personal, handheld pedi device that offers two levels of abrasion in one unit so that the user can, for example, first remove the roughest layer of skin using a rougher abrasive surface, then quickly switch to a less abrasive surface to smooth or polish the skin to its final fully exfoliated and groomed state.

SUMMARY OF THE INVENTION

It is an object of the present invention to provide a handheld, skin exfoliating apparatus that has a handle portion to be held by a user, a head portion connected to the handle portion and having two drums with different abrasiveness mounted on opposite sides of the head portion, as well as a drive motor and gears to rotate the drums for exfoliate skin when a respective outer surface of one drum contacts the skin so that the user can quickly and easily switch from exfoliating the skin, for example rough skin on the heel of the user's foot, using a rougher abrasiveness, to using less rough abrasiveness for smoothing the skin.

According to the invention, the more abrasive drum is preferably a mineral roller that operates at a speed of 2,000 rpm or more to loosen, lift, and roll away calluses from the feet or hands. The less abrasive drum, also operating at a speed of 2,000 rpm or more, is then used to smooth and polish the skin.

Two embodiments for the drive means or mechanism of the invention is also disclosed.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
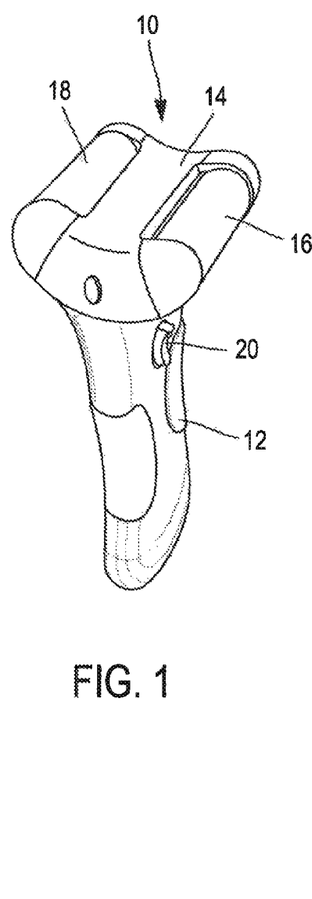
FIG. 1 is a top perspective view of a handheld skin exfoliating apparatus of the invention showing the handle and connected head portions thereof.

Referring now to the drawings, in which like reference numerals are used to refer to the same or similar elements, FIG. 1 illustrates a handheld skin exfoliating apparatus 10 that comprises a handle portion 12 adapted to be held in the hand of a user, a head portion 14 connected to the handle portion and having opposite sides.

A first drum 16 having a first outer surface is mounted for rotation to the head portion 14 with at least part of the first outer surface of the first drum being exposed at one side of the head portion 14 so that is can contact an area of skin to be exfoliated.

In accordance with the advantages of the invention, the apparatus also includes second drum 18 having a second outer surface, the second drum being mounted for rotation to the head portion 14 with at least part of the second outer surface being exposed at the opposite side of the head portion.

Also in accordance with the advantages of the invention, the first drum's outer surface is abrasive to the skin of the user and has a first level of abrasiveness, while the second drum's outer surface is also abrasive to the skin of the user but has a second level of abrasiveness that is different from the first level of abrasiveness. In one embodiment of the invention the first drum 16 that is meant to be used first to remove rougher skin, e.g. callused skin, has a higher or greater level of abrasiveness than the second drum 18 that is meant to be used second to smooth and polish the skin, and that has a lower or lesser level of abrasiveness.

As illustrated by FIGS. 4 to 8, the apparatus also includes drive means mounted to head portion 14 and operatively connected to each drum 16 and 18 for rotating each drum at a rotation rate sufficient to exfoliate skin when the respective first and second outer surface contacts the skin.

In this way rotating the drums exfoliates the skin when a respective outer surface of one drum contacts the skin so that the user can quickly and easily switch from exfoliating the skin, for example rougher skin on the heel of the user's foot using the rougher abrasiveness to remove rougher skin, to using the lower level of abrasiveness to smooth and polish the skin by simply flipping the head portion, end-for-end. During this entire operation the power may stay on, e.g. but activating a slide switch 20 on the handle portion 12, and leaving it in an ON position until both drums have been used on the skin, or the switch 20 may be a push button switch that rotates the drums only when the switch is pushed.

Figure 4:
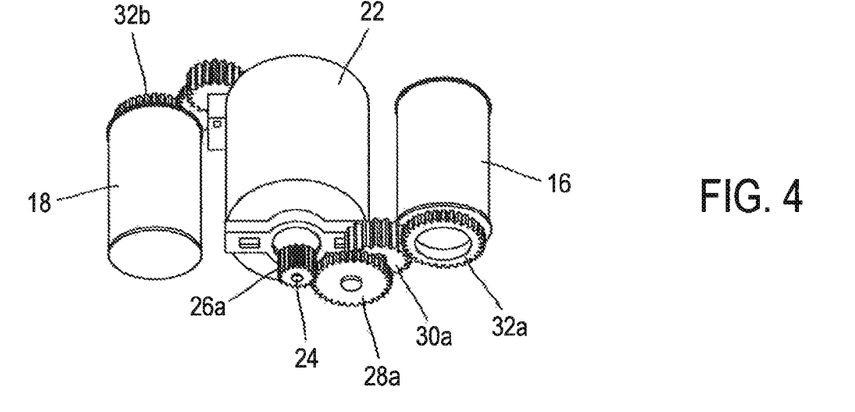
FIG. 4 is a perspective view of drive means of the apparatus which includes a motor and gear trains, FIG. 4 also illustrating the dual abrasive drums of the apparatus that are rotated by the drive means.
Figure 5:
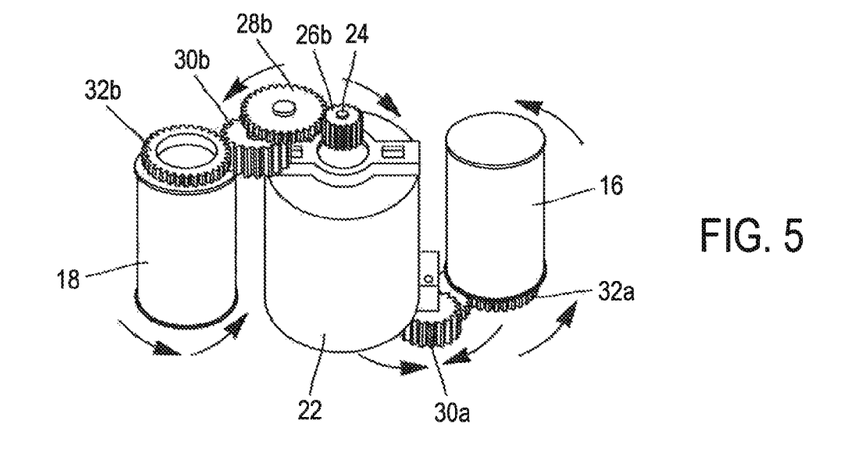
FIG. 5 is a perspective view similar to FIG. 4 but from an opposite side.
Figure 6:
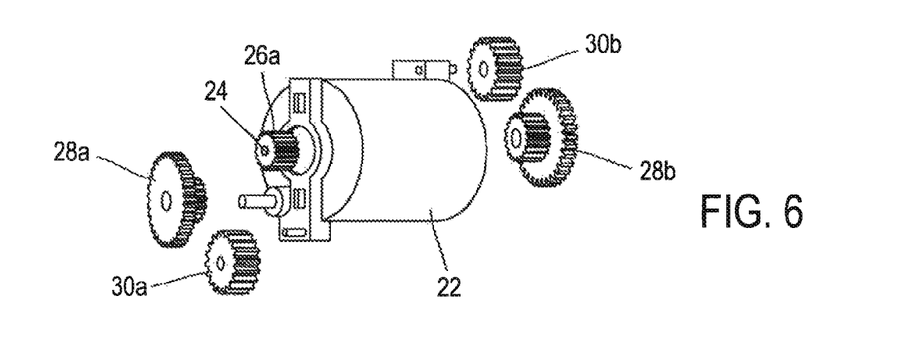
FIG. 6 is an exploded view of the motor, gear trains and dual abrasive drums of the apparatus.

As best shown in FIGS. 4 to 6, the drive means comprises a motor 22 having a shaft 24 extending through and beyond both sides of the motor housing, each shaft end having a shaft gear 26a and 26b fixed thereto, for rotation in the same direction when the motor 22 is powered. This occurs when switch 20 is slide, pressed or otherwise moved to an ON position, to close a power circuit and power supply, such as a rechargeable battery in housing 12. Any switching and/or powering mechanism may be used, however. For example, a simple spring-loaded push button switch may be used so the user must always keep the button pressed to power the motor and rotate the drums. Power may be supplied by wall current only without using batteries, or exchangeable non-rechargeable batteries may be used in handle portion 12.

The drive means includes a double gear on either side of the motor, shown at 28a and 28b, each double gear having a large diameter tooth portion meshed to a shaft gear 26a or 26b, and a small diameter toothed portion meshed with an intermediate gear 30a and 30b. Each intermediate gear is then meshed with a drum gear 32a and 32b.

In this embodiment of the drive means, rotation of shaft 24 in one direction causes rotation of both drums 16 and 18 in the same direction and at the same speed. In the embodiment illustrated, the gear ratios are selected to impart a rotational speed to the drums of about 2,500 rpm, or in the preferred range of 2,000 to 3,000 rpm. The preferred rpm gear ratio of the motor shaft to the drums is 6:1. It is understood that the invention may embodiment different drive mechanisms and different gear ratios to rotate the drums at different speeds and in the same or in opposite directions.

The material used for the gears is plastic, preferably POM (polyoxymethylene) although metals such as brass or fiber reinforced composites or other materials may be utilized.

Drums 16 and 18 may be plastic cylinders onto which grit, such as sand or other granular mineral is glued. As is well known in the art, sand of different particle sizes, roughness and other characteristics can be used to impart any desired level of abrasiveness to each drum. According to the invention different abrasiveness is applied to each of drums 16 and 18 so that the user can select the level of abrasiveness desired for a particular part of the exfoliation process.

Any known material for the grit, substrate or other parts of the invention can be utilized as may be selected for a particular application.

Figure 2:
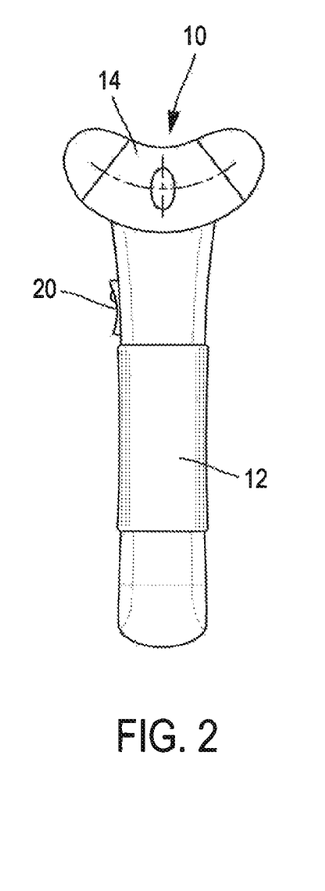
FIG. 2 is a front view of the apparatus.
Figure 3:
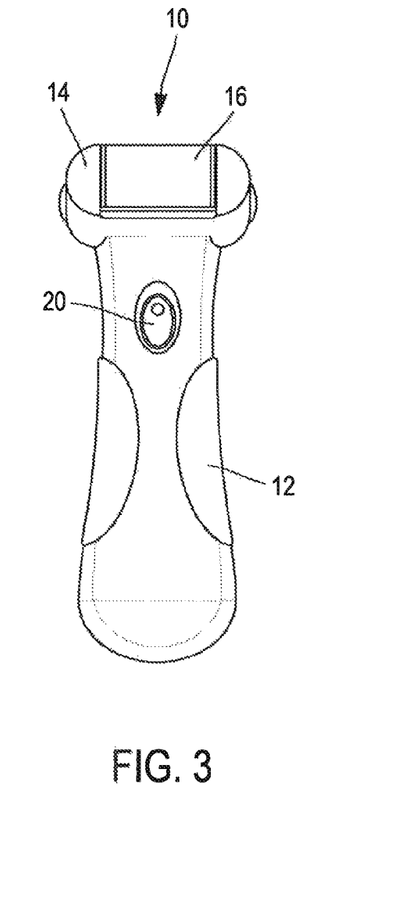
FIG. 3 is a side view of the apparatus, the opposite side being similar but with a drum of different abrasiveness and no control switch.
Figure 7:
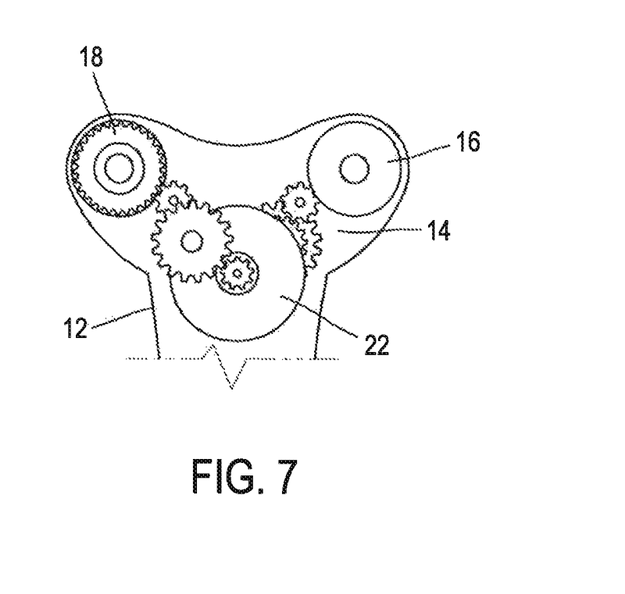
FIG. 7 is a front view showing the drive means and drums mounted in the head portion of the apparatus.
Figure 8:
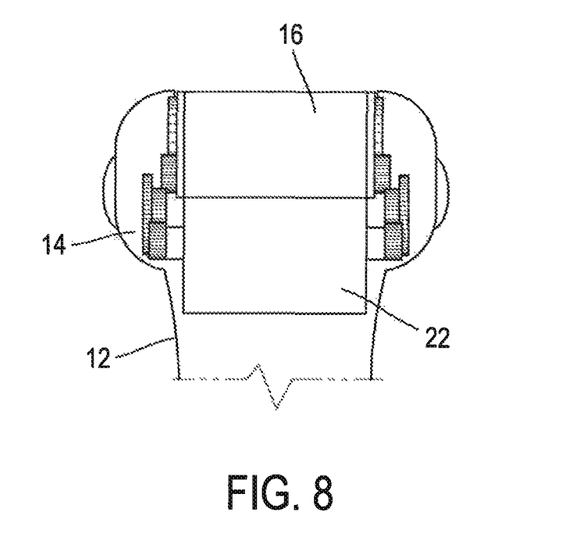
FIG. 8 is a side view showing the drive means and drums mounted in the head portion of the apparatus.

As best illustrated in FIGS. 1, 2, and 7, the head portion 14 is advantageously curved in a plain transverse of the major axis of the handle portion 12, so that the opposite ends of the head portion 14 and therefore the drums carried within this head portion, are forward of a central part of the head portion 14 so that, during use, more of the exposed abrasive circumference of each drum 16 and 18 are available for use by the user, to contact skin to be exfoliated.

In any number of alterative designs that fall within the scope of the invention, the drive means may be mounted in the handle portion or partly in the head and handle portions, and may be embodied in any form to rotate the drums 16 and 18, either together or apart, in the same or opposite directions and at the same or different speeds.

First drum 16 of greater or a higher level of abrasiveness comprises a cylinder of plastic, cardboard, metal or other material, with an outer surface or substrate of the same a different material, on which is glued or otherwise adhered grit, granules or particles to create an abrasive surface.

The substrate may be paper, cloth such as cotton, polyester, rayon or other cloth, plastic such as PET film, mylar or other material.

The grit, granules or particles for drum 16 may be of one or more of: sand, flint, garnet, emery, aluminum oxide, silicon carbide, alumina-zirconia, chromium oxide, ceramic aluminum oxide, or other abrasive particle.

The practical size and material of the grit, granules or particles for drum 16 are selected to give the outer surface of drum 16 a roughness in ISO/FEPA grit designation, of about P12 to about P220.

Second drum 18 of less or a lower level of abrasiveness comprises a cylinder of the same or different material a drum 16, also with an outer surface or substrate of the same a different material, on which is glued or otherwise adhered grit or particles to create an abrasive surface.

The grit or particles for drum 18 may also be of one or more of: sand, flint, garnet, emery, aluminum oxide, silicon carbide, alumina-zirconia, chromium oxide, ceramic aluminum oxide, or other abrasive particle.

The practical size and material of the grit or particles for drum 18 are selected to give the outer surface of drum 18 a roughness in ISO/FEPA grit designation of about P240 to about P6000.

Other ranges of abrasiveness may be used for drums 16 and 18, as long as they are different. The preferred embodiment of the invention uses course quartz sand as the abrasive particles for drum 16 of higher abrasiveness at a roughness level of about 40 pcs to about 75 pcs or preferably 60 pcs sand, and fine quartz sand as the abrasive particles for drum 18 of lower abrasiveness at a roughness level of about 80 pcs to about 115 pcs or preferably about 100 pcs sand.

With reference to FIGS. 9 to 13 a second embodiment of the invention comprises a handheld skin exfoliating apparatus 110 having a handle portion 112 adapted to be held in the hand of a user and a head portion 114 connected to or formed as one piece with the handle portion and having opposite sides.

Figure 9:
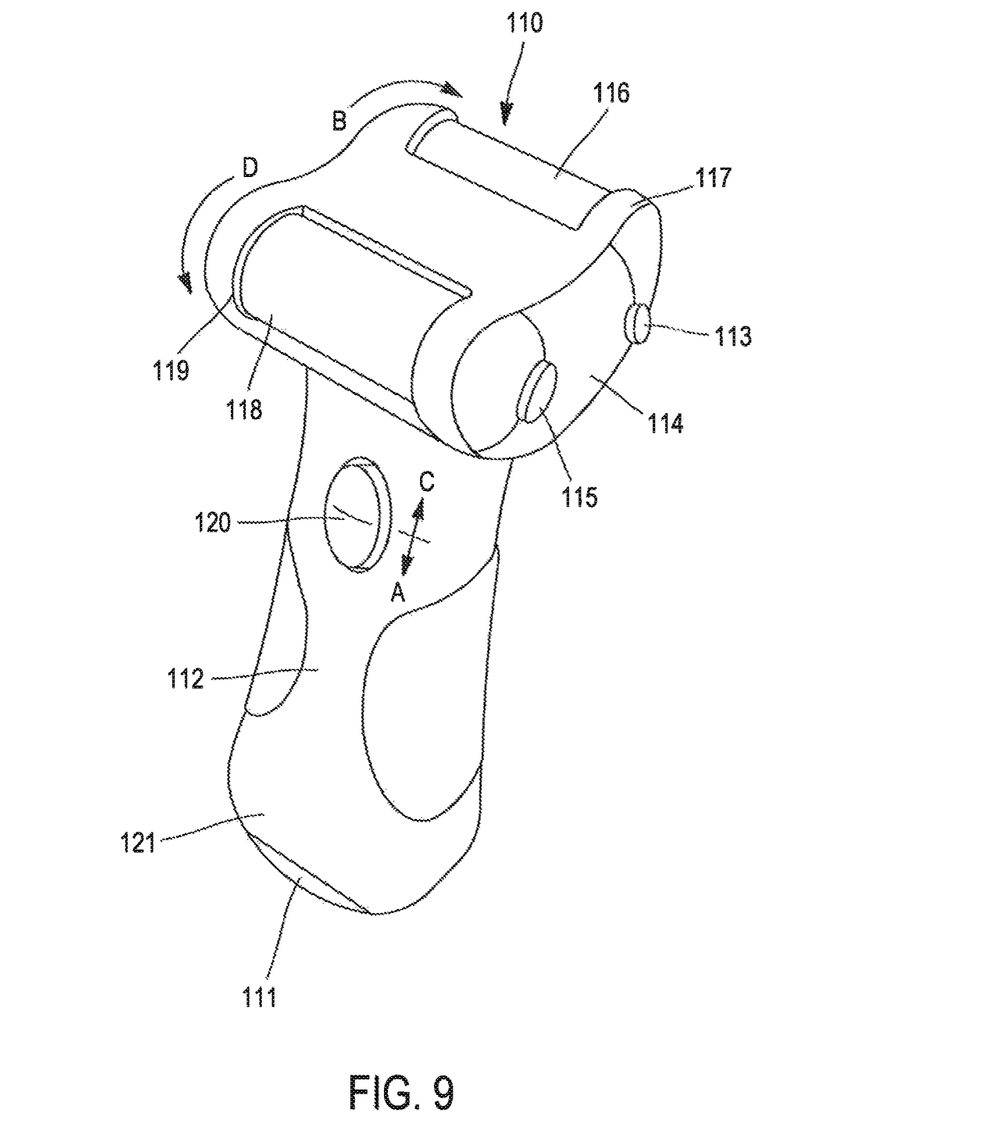
FIG. 9 is a top perspective view of a second embodiment of the handheld skin exfoliating apparatus of the invention.
Figure 10:
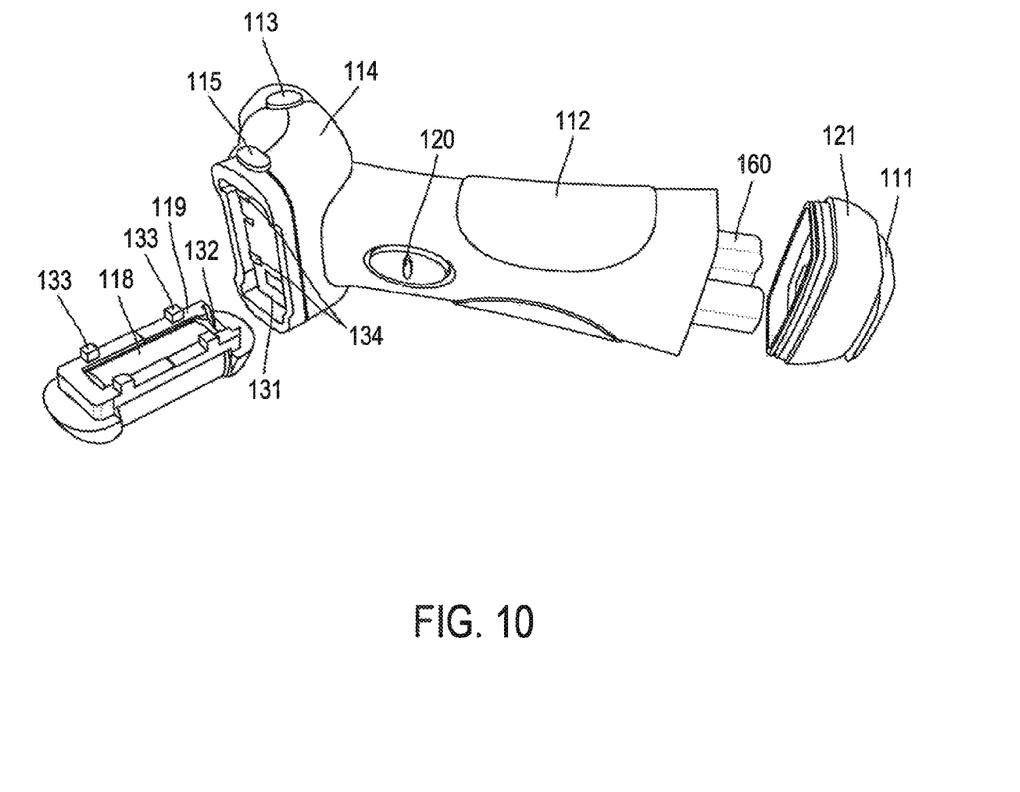
FIG. 10 is a side perspective view of the second embodiment with one of the abrasive drum assemblies removed.

A first drum 116 having a first outer surface of a first lower abrasiveness is mounted for rotation in a first drum assembly 117 that is detachably connected via a first release button 113, to one side of the head portion 114, with at least part of the first outer surface being exposed at one of the sides of the head portion.

In likewise fashion, a second drum 118 having a second outer surface of higher abrasiveness is mounted for rotation in a second drum assembly 119 that is detachably connected via a second release button 115, to the opposite side of the head portion 114, also with at least part of the second outer surface being exposed at the opposite side of the head portion.

Figure 11:
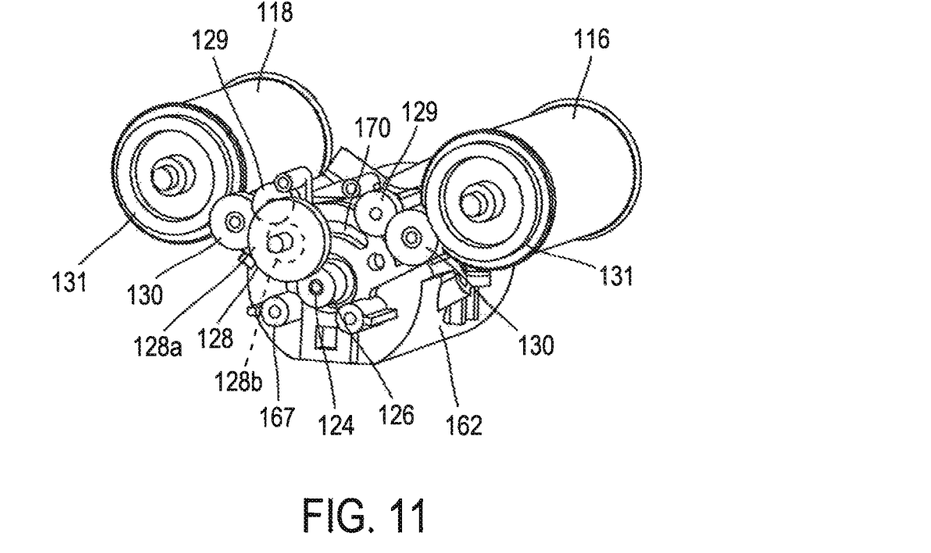
FIG. 11 is a perspective view of the drive means with two drums of the second embodiment.
Figure 12:
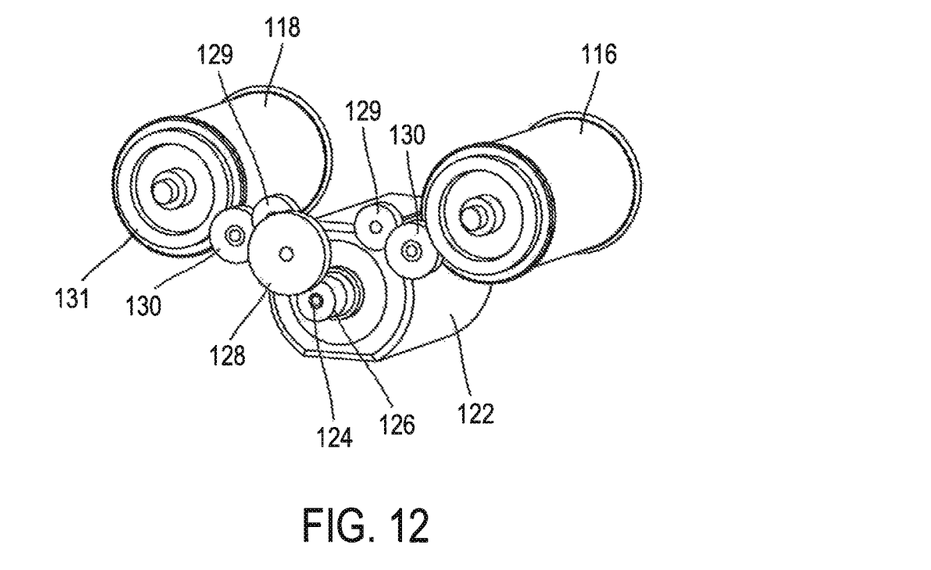
FIG. 12 is a perspective view of the drive means with two drums of the second embodiment, but with the motor housing removed to show the electric motor of the mechanism.
Figure 13:
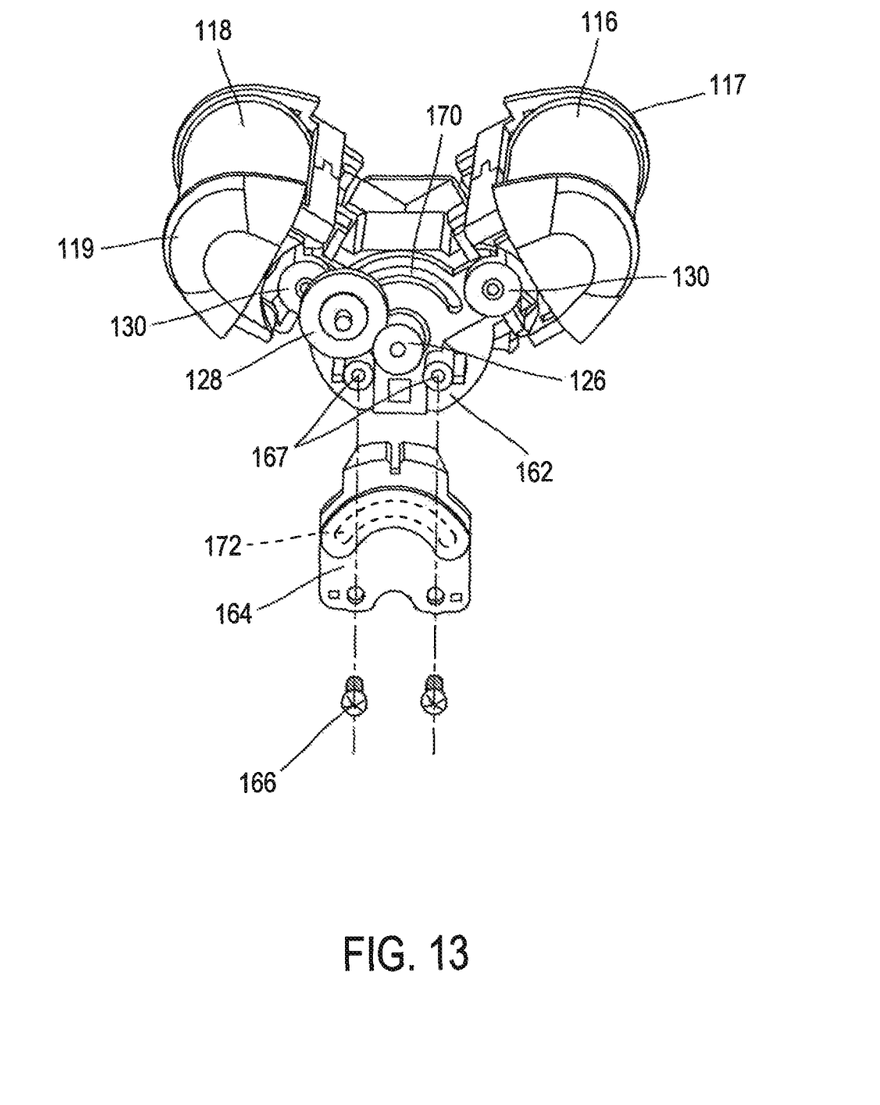
FIG. 13 is a partly exploded perspective view of the second embodiment drive means with two drum assemblies.

Drive means shown in FIGS. 11 to 13 are mounted in the head portion and are operatively connected to each of the first and second drums 116, 118, for rotating each drum at a rotation rate sufficient to exfoliate skin when the respective first and second outer surface contacts the skin. Rotation rates and abrasiveness and materials for the abrasive drum surfaces are the same as for the first embodiment.

With reference to FIGS. 9 and 10, a pair of batteries, e.g. AA batteries 160, are housed in side-by-side manner in the handle portion 112 which has a bottom opening for receiving the batteries, that is covered by an end cap 121 and latch 111 that pivots 90 degrees from a closed and locked position shown in FIG. 9, to lock the cap and battery compartment closed, to an open, unlocked position shown in FIG. 10, with the cap 121 removed to allow access for the batteries to be inserted into and removed from the battery compartment.

The batteries power a single, reversible, DC motor 122 shown in FIG. 12, in the drive means. When slide switch 120 is pulled downwardly in the direction of arrow A in FIG. 9, the motor is powered in a polarity to make its shaft 124 in FIG. 12, to rotate in one direction that operates a gear train to rotate drum 116 in direction B, i.e. downwardly toward the handle portion 112.

Conversely, when slide switch 120 is pushed upwardly in the direction of arrow C in FIG. 9, the motor is powered in a reverse polarity to make its shaft 124 rotate in the opposite direction that operates the gear train to rotate drum 118 in direction D, i.e. also downwardly toward the handle portion 112.

As will be explained, the gear train has a swinging gear arrangement that engages the gears for one drum while disengaging the gears for the other drum, allowing it to be unpowered and to rotate freely. In this way, only the powered drum rotates in direction B or D, while the other drum is unpowered but is free to rotate on its bearings in its drum assembly.

FIG. 10 also illustrated the function of release buttons 113 and 115. Each drum assembly 117 and 119, has a lower surface with four hooks 133, shown for assembly 119, that can engage in four corresponding openings 134 in a mating surface of head portion 114, for receiving the lower surface of the drum assembly. Pushing in on button 115 will move spring-loaded stops (not shown) in the head portion 114, out from under each hook 133 to release the assembly 119. When the button 115 is released, while the assembly 119 is in place on head portion 114, the stops engage under hooks 133 and the drum assembly is locked to the head portion. In this way each drum assembly 117 and 119 can be selectively attached to and removed from the head portion 114, e.g. for cleaning or replacement.

Referring now to FIGS. 11-13, the drive means of the second embodiment comprises motor 122 in a motor housing 162. Motor 122 has a single motor shaft 124 that has a shaft gear 126 fixed thereto. Shaft gear 126, extends outwardly of one end of housing 162 and has teeth that engage the teeth of a larger gear 128a of a double gear 128 mounted for rotation on a swinging shaft 140. Swinging shaft 140 has opposite ends that extend past the double gear 128 on both sides and that are rotatably and slidably carried in a pair of curved channels 170 and 172. Channel 170 is a curved slot in the front face of motor housing 162 and channel 172 is a covered channel in housing cover 164 that is attached over the gear set of the drive means by a pair of screws 166, threaded into posts 167 formed as one piece with housing 162. Channels 170 and 172 are greased or otherwise lubricated so that swing shaft 140 may easily slide back and forth along the channels.

In operation, when switch 120 is slide up or down to activated one of the drums 116 or 118, the motor shaft 124 is caused to rotate either clock-wise or counter-clock-wise. When rotating counter-clock-wise, shaft gear 126, since it is engaged with larger gear 128a, will cause the double gear 128 to swing and slide to the left in FIGS. 11 and 12, and cause its smaller gear 128b to engage the teeth of a first intermediate gear 129 that is mounted for rotation to housing 162. Once seated at the left end of channels 170, 172, larger gear 128a will rotate clock-wise and cause first intermediate gear 129 to rotate counter-clock-wise. This causes a second intermediate gear 130, that is engaged to the teeth of first intermediate gear 129, to rotate clock-wise, and transmit its rotation to counter-clock-wise rotation of a drum gear 131, fixed to drum 118, thereby causing drum 118 to rotate counter-clock-wise at a rate that is determined by the gear ratio established by the diameters and tooth spacing of gears 126, 128a, 128b, 129, 130 and 131, and the rotation speed of motor shaft 124.

Since the right side gears 129 and 130 are not engaged to the double gear 128 in this activation of the left hand drum 118, the right hand drum 116 in FIGS. 11 and 12 is unpowered and free to rotation. To activation drum 116, switch 120 is slide in the opposite direction. This reverses the rotation direction of shaft 124, causing double gear 128 to swing to the right, disengage from the left side gear 129, and engage the right side gear 129 at the opposite end of channels 170 and 172.

In FIG. 13 the same drive means as in FIGS. 11 and 12 is illustrated, except that only one intermediate gear 130 in each side of the gear train is used, rather than two.

While specific embodiments of the invention have been shown and described in detail to illustrate the application of the principles of the invention, it will be understood that the invention may be embodied otherwise without departing from such principles.

What is claimed is:

1. A handheld skin exfoliating apparatus comprising:
a handle portion adapted to be held in a hand of a user;
a head portion connected to the handle portion and having opposite sides;
a first drum having a first outer surface, the first drum being mounted for rotation to the head portion with at least part of the first outer surface being exposed at one of the sides of the head portion;
a second drum having a second outer surface, the second drum being mounted for rotation to the head portion with at least part of the second outer surface being exposed at an opposite one of the sides of the head portion;
the first outer surface being abrasive to skin of the user and having a first level of abrasiveness;
the second outer surface being abrasive to the skin of the user and having a second level of abrasiveness that is different from the first level of abrasiveness; and
drive means mounted to at least one of the handle and head portions, the drive means operatively connected to each of the first and second drums for rotating each drum at a rotation rate sufficient to exfoliate the skin when respective ones of the first and the second outer surface contacts the skin,
the drive means further comprising a motor having a shaft with an end extending beyond a side of the motor, and a gear train engaged between the end of the shaft and a respective one of the drums, the gear train comprising a shaft gear connected to the end of the shaft, a double gear having a large diameter portion meshed with the shaft gear and a small diameter portion, the double gear being rotatably mounted on a swinging shaft, the swinging shaft being slidably and rotatably carried in at least one channel, whereby the double gear swings between opposite operative positions on each one of the opposite sides of the head portion, an intermediate gear being located at each one of the sides of the head portion, each one of the intermediate gears being alternatingly meshed with the small diameter portion of the double gear when the double gear swings to each of the operative positions at respective ones of the sides of the head portion, and a drum gear connected to each drum, each drum gear meshed with a respective one of the intermediate gears;

wherein the head portion is curved in a plane transverse to a major axis of the handle portion so that the opposite sides of the head portion and the drums which are carried within the head portion are forward of a central part of the head portion to better expose the outer surfaces of the drums in use.

2. A handheld skin exfoliating apparatus comprising: a handle portion, a head portion connected to the handle portion, two drums having different abrasiveness mounted on opposite sides of the head portion and a drive motor mounted to at last one of the handle and head portions, the drive motor operatively connected to the drums to rotate the drums to exfoliate skin when a respective outer surface of each one of the drums contacts the skin, wherein the drive motor comprises a shaft with an end extending beyond a side of the motor, and a gear train engaged between the end of the shaft and a respective one of the drums, the gear train comprising a shaft gear connected to the end of the shaft, a double gear having a large diameter portion meshed with the shaft gear and a small diameter portion, the double gear being rotatably mounted on a swinging shaft, the swinging shaft being slidably and rotatably carried in at least one channel, whereby the double gear swings between opposite operative positions on each one of the opposite sides of the head portion, an intermediate gear being located at each one of the sides of the head portion, each one of the intermediate gears being alternatingly meshed with the small diameter portion of the double gear when the double gear swings to each of the operative positions at each of the sides of the head portion, and a drum gear connected to each drum, each drum gear meshed with a respective one of the intermediate gears;

wherein the head portion is curved in a plane transverse to a major axis of the handle portion so that the opposite sides of the head portion and the drums which are carried within the head portion are forward of a central part of the head portion to better expose the outer surfaces of the drums in use.

3. The apparatus of claim 2, wherein the drive motor is mounted in an area where the head and handle portion connect to each other.

4. The apparatus of claim 2, wherein the drive motor is located in the head portion.

\* \* \* \* \*